(12) United States Patent
Miethe et al.

(10) Patent No.: US 8,071,027 B2
(45) Date of Patent: Dec. 6, 2011

(54) METHOD AND DEVICE FOR SELECTIVELY DETECTING FERROMAGNETIC OR SUPERPARAMAGNETIC PARTICLES

(75) Inventors: Peter Miethe, Schleberoda (DE); Hans-Joachim Krause, Baesweiler (DE); Yi Zhang, Jülich (DE); Norbert Wolters, Herzogenrath (DE); Dmitry Plaksin, Baesweiler (DE)

(73) Assignee: Forschungszentrum Juelich GmbH, Juelich (DE)

( * ) Notice: Subject to any disclaimer, the term of this patent is extended or adjusted under 35 U.S.C. 154(b) by 1212 days.

(21) Appl. No.: 10/547,444

(22) PCT Filed: Jan. 30, 2004

(86) PCT No.: PCT/DE2004/000149
§ 371 (c)(1),
(2), (4) Date: Feb. 9, 2007

(87) PCT Pub. No.: WO2004/077044
PCT Pub. Date: Sep. 10, 2004

(65) Prior Publication Data
US 2007/0155024 A1   Jul. 5, 2007

(30) Foreign Application Priority Data
Feb. 28, 2003   (DE) ................... 103 09 132

(51) Int. Cl.
*G01N 15/06* (2006.01)
*G01V 3/08* (2006.01)

(52) U.S. Cl. ................ 422/68.1; 324/326

(58) Field of Classification Search ........... 422/68.1; 324/326
See application file for complete search history.

(56) References Cited

U.S. PATENT DOCUMENTS

| | | | |
|---|---|---|---|
| 5,001,424 A | 3/1991 | Kellett et al. | |
| 5,005,001 A | 4/1991 | Cordery | |
| 5,925,573 A | 7/1999 | Colin et al. | |
| 6,005,443 A * | 12/1999 | Damgaard et al. | 331/14 |
| 6,046,585 A | 4/2000 | Simmonds | |
| 6,201,391 B1 | 3/2001 | Burkhardt et al. | |
| 6,437,563 B1 * | 8/2002 | Simmonds et al. | 324/239 |

(Continued)

FOREIGN PATENT DOCUMENTS

DE            10137665 A     11/2002
(Continued)

*Primary Examiner* — Mark Shibuya
*Assistant Examiner* — Pensee Do
(74) *Attorney, Agent, or Firm* — Andrew Wilford

(57) ABSTRACT

The invention relates to a method for selectively detecting and/or quantifying superparamagnetic and/or ferromagnetic particles on analytes. The method is characterized in that a frequency component of magnetic fields (15, 18), which is generated due to the non-linearity of the magnetization characteristic curve of the particles, is measured at a mixing frequency. A device for selectively detecting and/or quantifying superparamagnetic and/or ferromagnetic particles on analytes comprises: a container (12) that contains particles, which are to be detected and/or quantified, on analytes; at least one oscillator (13, 16; 25) for generating frequencies of alternating magnetic fields (15, 18); at least one field generator (14, 17) for subjecting the analytes to alternating magnetic fields (15, 18); a magnetic field sensor (20) for measuring a response magnetic field (19) of the particles, and; at least one phase-sensitive detector (21, 23). These elements are configured in such a manner as to enable a frequency component of the magnetic fields (15, 18), which is generated due to the non-linearity of the magnetization characteristic curve of the particles, to be measured at a mixing frequency.

15 Claims, 4 Drawing Sheets

(a)

(b)

U.S. PATENT DOCUMENTS 6,597,176 B2 * 7/2003 Simmonds et al. ........... 324/326
6,825,655 B2 * 11/2004 Minchole et al. ............. 324/204
2003/0210040 A1 * 11/2003 Kang et al. .................... 324/228

FOREIGN PATENT DOCUMENTS

| DE | 101 26 940 | 12/2002 |
| --- | --- | --- |
| EP | 1262766 | 12/2002 |
| EP | 1262766 A2 * | 12/2002 |
| GB | 1 603 578 | 11/1981 |
| JP | 59040287 | 3/1984 |
| SU | 543902 B | 1/1977 |
| WO | WO 00/49407 | 8/2000 |

* cited by examiner

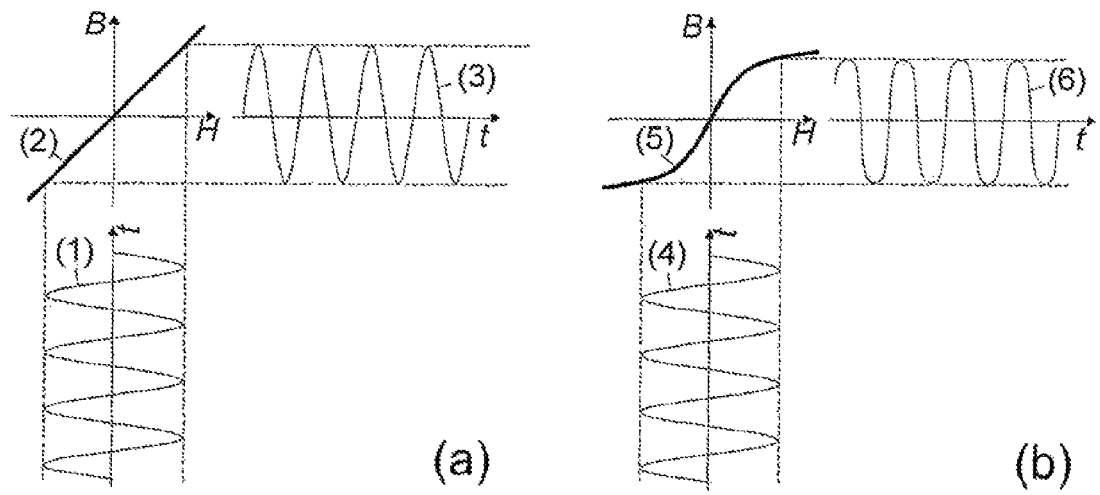
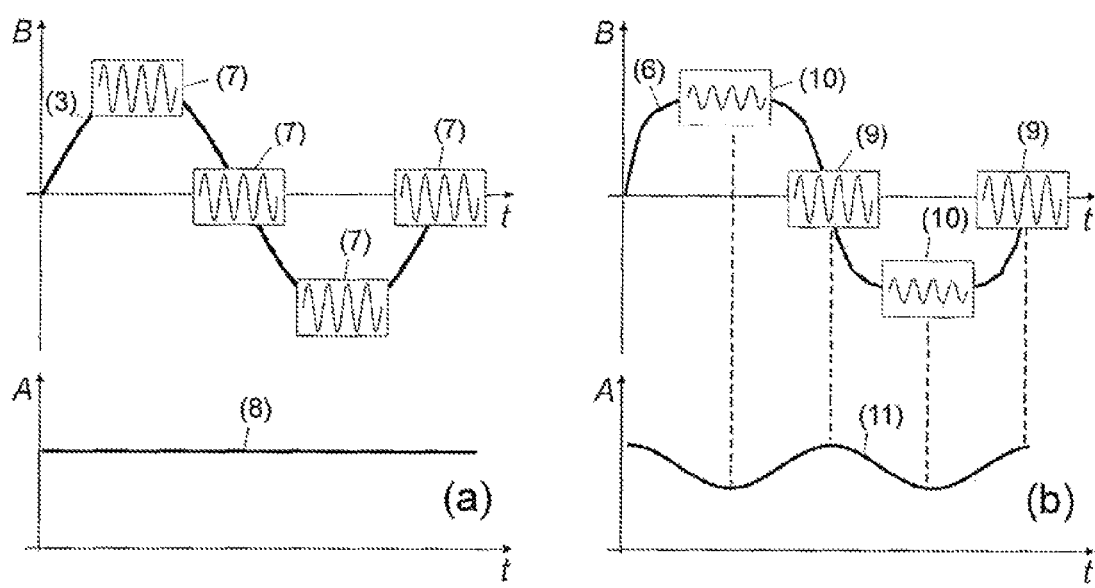
Fig. 1
Fig. 2

METHOD AND DEVICE FOR SELECTIVELY DETECTING FERROMAGNETIC OR SUPERPARAMAGNETIC PARTICLES

CROSS REFERENCE TO RELATED APPLICATIONS

This application is the US-national phase of PCT application PCT/DE2004/000149 filed 30 Jan. 2004, published 10 Sep. 2004 as WO2004/077044, and claiming the priority of German patent application 10309132.7 itself filed 28 Feb. 2003, whose entire disclosures are herewith incorporated by reference.

FIELD OF THE INVENTION

The invention relates to the detection of magnetic particles as markers in analytes.

BACKGROUND OF THE INVENTION

From the state of the art, detection processes with analytes by means of fluorochromes, enzymes or radioactive particles as so called markers for analytes are known. It is a drawback that the linear detection range of fluorescent markers or the sensitivity of enzymatic techniques are limited. Radioactive markers are problematical because of the need to provide radiation protection.

Bioassays on the basis of magnetic marking of analytes is therefore one alternative. The magnetic particles are comprised of an iron oxide core with a defined diameter of several tens of nanometers to several hundred nanometers. They have a biocompatible surface coating with which they can bond to the analytes, for example, to chemical substances, or to the surfaces of cells or viruses in a manner known per se.

Advantageously, such markers are stable, nontoxic and manipulatable by means of magnetic fields. Particles of iron oxide are superparamagnetic. The presence of magnetic particles in a sample volume can be determined by alternating field susceptometry. In the case of monodispersitates, i.e. a unitary particle size, the concentration of the particles can also be quantitatively determined.

From U.S. Pat. No. 6,110,660 the detection of magnetic particles by means of susceptometry is known. In that case the magnetic susceptibility of an analyte is measured by means of a Maxwell bridge in the frequency range around 200 kHz. The measured electrical voltage on an output amplifier of the bridge is proportional to the susceptability of the solution. With constant particle size, the susceptibility is also proportional to the number of magnetic particles in solution.

The drawback is that this method is not selective. Indeed the magnetic susceptibility of concentrated nanoparticle solutions is high. However, immunoassay methods as a rule detect very small concentrations of biomolecules and consequently very small concentrations of magnetic marker particles. The resulting susceptibility of the solution is then very small and can hardly be distinguished from the susceptibility of a control solution or blank without magnetic particles. To increase the amplification at the output of the Maxwell bridge is hardly a usable solution to this problem because of parasitic effects like susceptibility variations in the sample vessel, the reagents and the laboratory environment as well as the spread in the output voltage give rise like thermal effects and electrical drifting of the components of the readout circuit interfere.

From U.S. Pat. No. 6,046,585, the movement of magnetic particle samples to produce a low frequency modulation of the measurement signal using a qradiometric SQUID magnetic field detector is known. The drawback here is that signals from the sample holder and the sample vessel cannot be suppressed in this process.

OBJECT OF THE INVENTION

It is the object of the invention, therefore, to provide a method for selectively detecting superparamagnetic particles and/or ferromagnetic particles so as to allow such particles to be detected in a highly sensitive manner with low apparatus costs. It is another object of the invention further to provide a device for carrying out the method.

SUMMARY OF THE INVENTION

For the selective detection and/or for quantifying superparamagnetic and/or ferromagnetic particles, because of the nonlinearity of the magnetization characteristics of the particles frequency components of the magnetic fields with a mixed frequency are measured. Superparamagnetic and ferromagnetic substances have a nonlinear magnetization characteristic line which is a characteristic used in accordance with the invention for the selective detection of these substances. The method utilizes the dependency of the differential susceptibility (that is the derivative of the magnetic susceptibility) upon the magnetic field acting on the particles.

The particles are subjected to a first alternating magnetic field. This has the consequence of modulating the magnetization characteristic line of the particles (modulating magnetic field).

Preferably the modulating magnetic field has a frequency between 50 and 100 Hertz. By selecting such low frequency alternating magnetic fields, low currents and voltages can be used.

In addition, the particles are subjected to a second alternating magnetic field with a different frequency from that of the modulating magnetic field. The second alternating field serves for scanning the nonlinearity of the magnetizing field characteristic line of the particles (scanning or exploring magnetic field).

As a consequence, as a result of the effects of the first alternating magnetic fields, there is an induced response magnetic field of the magnetic particles which can be measured.

The scanning magnetic field can advantageously have a frequency between 10 and 100 kilohertz. For this purpose when an induction coil is advantageously used as a magnetic field sensor, a voltage is induced by the response magnetic field in this coil which is proportional to the frequency of the response magnetic field, is relatively high and thus is easily measurable.

The amplitude variation which arises from the response magnetic is primarily dependent upon the type or concentration of the magnetic particles. Superparamagnetic and ferromagnetic materials have, as previously indicated, a nonlinear magnetization characteristic based upon the nonlinear magnetization characteristic material which can be selectively detected.

The response magnetic field has at a sensor mixed frequency components of the two alternating magnetic fields applied to the magnetic particles. One such component can be detected by suitable phase sensitive detection (demodulation). The voltage thus produced corresponds to the amplitude course of the component and is part of the output signal or is the output signal for determining the concentration of the analyte.

It has been found to be especially advantageous to measure the time course of the amplitude (amplitude variation) of the response magnetic field by phase sensitive detection of the frequency of the response magnetic field.

In the case of superparamagnetic and ferromagnetic analytes, the time course of the amplitude of the magnetic field will show frequency components which are a multiple of the frequency of the modulating magnetic field. Especially pronounced are even multiples and especially the component with the double frequency of the modulating magnetic field.

The reason for this is that the modulating magnetic field results in a distorted magnetic induction of the magnetic particles. The additionally applied scanning magnetic field has, in the case in which the modulating magnetic field has an instantaneous magnetic induction in a zero pass, the consequence that a large additional magnetic induction will result. In the case in which the modulating induction is at a maximum. The scanning magnetic field by contrast contributes only to a small additional induction. The amplitude is monitored by the derivative of the magnetization curve of the magnetic particles which in the case of large magnetic fields, because of the saturation effect, is smaller than in the case of smaller magnetic fields. If one considers the time course of the amplitude of the response magnetic field to the frequency of the scanning magnetic field as a function of time, one finds that this amplitude varies directly with twice the frequency of the frequency of the modulating magnetic field. It has its minimum at the extremes of modulation and its maximum at the zero passes.

The amplitude variation of the response magnetic field is demodulated by phase sensitive detection. The response magnetic field is converted in a magnetic field sensor to an electric voltage and optionally is amplified.

The resulting output voltage is in the case of monodispersed particles, advantageously linearly proportional to the concentration of the analyte which can be calculated after calibration of the measurement system.

A device for the selective detection and/or quantification of superparamagnetic and or ferromagnetic particles by means of differential of the susceptibility of the particles comprises a container or vessel for the analyte with the particles to be detected and/or quantified. The container can be composed of a nonmagnetic material suitable for the process. That is, for example, of glass or a synthetic resin (plastic).

The device comprises at least one oscillator. The oscillator is suitable for producing frequencies of alternating magnetic fields as are required for the present case.

Especially advantageously, the device comprises a basis frequency oscillator from which the frequencies of the scanning magnetic field and the modulating magnetic field are derived by means of frequency dividers in a phase-correct relationship.

However, also two oscillators can be used for the independent generation of both alternating magnetic fields. A first oscillator then produces the frequency of the scanning magnetic field, a second oscillator the frequency of the modulating magnetic field.

The device has at least one field generator. This serves for applying the alternating magnetic fields to the analyte or subjecting the analyte to the alternating magnetic fields. There can especially advantageously be two such field generators provided which subject the analyte to the first or second alternating magnetic field, that is the modulating magnetic field and the scanning magnetic field.

The device comprises a magnetic field sensor which serves to pick up a response magnetic field from the particles. The magnetic field sensor converts and amplifies the amplitude variation of the magnetic response of the particles and supplies to it to a phase sensitive detector for further processing.

The device comprises, in addition, at least one phase sensitive detector which is supplied from an oscillator optionally through a frequency divider with a reference frequency. The phase sensitive detector enables the amplitude of the response magnetic field to be determined at this frequency.

The device can encompass at least one second phase sensitive detector which is also fed by an oscillator, optionally through a frequency divider, with a reference frequency. In this case, the first phase sensitive detector advantageously supplied with the scanning frequency as the reference, supplies the amplitude of the response magnetic field at the scanning frequency. The second phase sensitive detector is supplied with a reference in the form of a multiple of the frequency of the modulating magnetic field. The second phase sensitive detector searches out the amplitude of the magnetic response field supplied by the first phase sensitive detector to the second phase sensitive detector for a frequency component which is an even number multiple, especially the double of the frequency of the modulating magnetic field. The second phase sensitive detector produces an output voltage corresponding to the amplitude of the frequency component.

To maximize the demodulated signal the device can further have phase shifters at the reference inputs of the phase sensitive detectors.

BRIEF DESCRIPTION OF THE DRAWING

In the drawing:

FIG. 1 is a diagram illustrating the instant invention;

FIG. 2 is a further diagram illustrating this invention;

SPECIFIC DESCRIPTION

Figure 3:
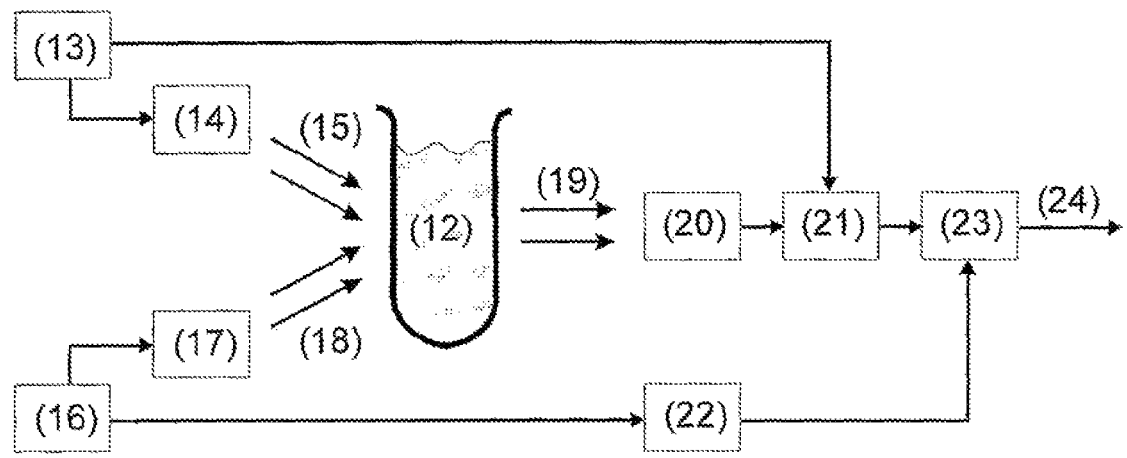
FIGS. 3, 4, and 5 are diagrammatic views illustrating the device of this invention.

FIG. 1 diagrammatically illustrates the basic physical characteristics of superparamagnetic and ferromagnetic materials. These materials have a nonlinear magnetization characteristic [magnetization characteristic line] (FIG. 1b). By contrast thereto, diagrammatic and paramagnetic materials have a linear magnetization characteristic (FIG. 1a).

The substances are excited with an alternating field of the frequency f and the amplitude $H_a$. A static or steady state magnetic field may additionally be applied, for example the Earths magnetic field and is designated $H_o$.

$$H(t) = H_a \sin(2\pi f t) + H_0 \tag{1}$$

FIG. 1a shows the magnetic modulating induction 3 of a paramagnetic substance on a modulating magnetic field 1. A paramagnetic substance is characterized by a constant permeability $\mu = \mu_0 \, \mu_r$ where $\mu_r$ is greater than 1.

$$\mu_0 = 4\pi \cdot 10^{-7} \frac{V_s}{Am}$$

The permeability of the vacuum is given by equation and $\mu_r$ represents the relative permeability count or coefficient of the material. The resulting magnetic modulating induction 3 is given by $$B(t) = \mu_0 \mu_r H_a \sin(2\pi f t) + \mu_0 \mu_r H_0 \tag{2}$$

which, as shown in FIG. 1a is an unmodified sinusoid. A paramagnetic material with a linear magnetization characteristic is supplied, therefore, an undistorted response. The same applies for diamagnetic materials with a constant relative permeability $$\mu_r < 1.$$

Superparamagnetic substances have the expected nonlinear and nonhysteretic magnetization characteristics 5. The magnetization M(H) of superparamagnetic substances can generally be described by the formula $$M(H) = M_S L\left(\frac{\mu_0 H}{B_c}\right) \quad (3)$$

In this equation $$L(x) = \coth(x) - \frac{1}{x} \quad (4)$$

which represents the Langevin function, $B_c$ the characteristic indication, $M_s$ the saturation magnetization of the particle and $$x = \frac{\mu_0 H}{B_C}$$

the argument of the Langevin function.

The typical magnetic response of a superparamagnetic material is shown as a distorted sin function for the magnetic modulation induction 6 in FIG. 1b and is generally described by inserting Formula (1) in Formula (3) as shown in Formula (5):

$$B(t) = M_S L\left(\frac{\mu_0}{B_c}[H_a \sin(2\pi f t) + H_0]\right) \quad (5)$$

According to the invention, a modulating magnetic field 4 is used to modulate the magnetization characteristic 5. The modulating magnetic field 4 is an alternating magnetic field of a certain frequency f.

In addition, the analyte is subjected to a second alternating field (not shown), a so-called scanning magnetic field. The frequency of the scanning magnetic field is selected to be different from the modulated magnetic field 4.

FIG. 2 shows the basic principle utilizing the method. FIG. 2b describes the case of a superparamagnetic or ferromagnetic analyte and FIG. 2a the case of a diamagnetic or paramagnetic analyte. The modulating magnetic field 4 as was illustrated in FIG. 2, gives rise to a distorted magnetic modulating induction 6 whose time dependency is described by the formula (5). The additional applied second alternating magnetic field gives rise, as a scanning magnetic field, in the case in which the modulating magnetic field generated magnetic modulated induction 6 passes through its zero point, to a large additional scanning induction at the frequency of this scanning magnetic field (FIG. 2, element 9).

In the case in which the induction 6 produced by the first alternating magnetic field (modulating magnetic field passes though a maximum), the scanning magnetic field leads only to a small additional induction (FIG. 2b, element 10).

The amplitude 11 of the response magnetic field can be monitored in terms of the derivative of the magnetization characteristic. In the case of superparamagnetic or ferromagnetic substances, this slope of the magnetization characteristic in the case of larger magnetic fields |H| is significantly smaller than originally at H=0. For superparamagnetic substances with a magnetization characteristic according to Equation 5 the derivative of the Langevin function gives $$\frac{dL(x)}{dx} = 1 - \coth(x)^2 - \frac{1}{x^2} \quad (6)$$

which for large |x| is significantly smaller than in the original with x=0.

If one sets the course of the amplitude 11 of the magnetic induction, that is the response magnetic field at the frequency of the scanning magnetic field as a function of time, one can see that this amplitude varies directly with twice the frequency of the modulating magnetic field 4. It has its minimum at the extremes and its maximum at the zero passages of the modulating magnetic field 4 is or the magnetic modulating induction 6. In the case of a paramagnetic analyte one obtains an undistorted magnetic induction 3 from the modulating magnetic field 1 because of the linear magnetization characteristic 2 in FIG. 1.

In that case, one obtains a uniform amplitude 8 of the additional induction 7 and independently of the scanning magnetic field or the value which the modulation magnetic field 1 or the modulating induction 3 may have (FIG. 2a, number 7).

The corresponding amplitude 8 of the magnetic induction at the frequency of the scanning magnetic field is constant with time.

Apart from the doubled frequency of the frequency of modulating magnetic field (or the modulating induction 6) the amplitude 11 of the modulating magnetic field 4 comprises at the frequency of the modulating magnetic field also higher harmonics of the frequency of the modulating magnetic field 4. At a symmetrical modulation the modulating characteristic 5, ($H_0$=0) one will find only frequency components with even number multiples of the frequency of the modulating field. If one considers an analyte to which is additionally applied a static direct field $H_o$, one will obtain additional frequency components with uneven multiples of the frequency of the modulating magnetic field.

The method has the advantage that only analytes with nonlinear magnetization characteristics will show a time variation in the amplitude 11 as illustrated in FIG. 2b. Paramagnetic or diamagnetic substances with linear magnetization characteristics 2 show a constant amplitude 8 of the magnetic induction of the frequency of the scanning magnetic field. This selectivity distinguishes the method of the invention from the methods of the state of the art which cannot distinguish whether a measured susceptibility derives from a diamagnetic or paramagnetic material or a superparamagnetic or ferromagnetic material.

FIG. 3 shows a first device for the selective detection and/or quantification of superparamagnetic and/or ferromagnetic materials in analytes. The components are so configured that based upon the nonlinearity of the magnetization characteristic 5 of the particles, frequency components of the magnetic fields 15 and 18 can be measured at a mixed frequency. Required for this purpose are a suitable vessel 12 and an analyte contained therein in a measurement volume. The analyte can be formed by a method known per se like a physisorption reaction, a chemisorption reaction, precipitation, filtration or extraction and introduced into the vessel 12. To the analyte detectable superparamagnetic and/or ferromagnetic particles are coupled.

An oscillator 16 generates the frequency of the modulating magnetic field 18 which is applied by means of a field generator 17 to the analyte.

An oscillator 13 generates the frequency of a second alternating magnetic field, the scanning magnetic field 15 which is applied by means of a further field generator 14 to the analyte.

The response magnetic field 19 which is emitted by the particles or the analyte is converted by a magnetic field sensor 20 into an electrical voltage and preamplified.

In addition, the device comprises a first phase sensitive detector 21 to which the frequency of the scanning magnetic field 15 from the oscillator 13 is fed has a reference. This phase-sensitive detector 21 outputs the time course of the amplitude (see FIG. 2 elements 11 or 8) of the response magnetic field 19 by the frequency of the scanning magnetic field 15. This amplitude 11 or 8 is fed to a second phase-sensitive detector 23 which is supplied by the oscillator 16 with the frequency of the modulating magnetic field 18 through an m-fold frequency multiplier 22 as a reference, to detect a frequency component which corresponds to the m-fold of the frequency of the modulating magnetic field with a whole positive number m. Preferably m is selected to be an even number and especially preferably m=2. The generated output voltage 24 corresponds to the amplitude of this frequency component. A frequency component is measured at a mixed frequency which only arises because of the presence of the nonlinearity in the magnetization characteristics of the particles.

To the extent that the detection chain 19-23 operates linearly, the output voltage 24 is linearly dependent upon the superparamagnetic/ferroparamagnetic moment in the sample volume of vessel 12.

At a constant moment of the individual magnetic particles in the analyte and constant measurement volume, the concentration of the magnetic marker in the sample is proportional to the output voltage. The amplitude of the modulating magnetic field is advantageously so chosen that the analyte will be driven in magnetic saturation. In the case of superparamagnetic particles, whose magnetization characteristic can be described by equation (3), the amplitude of the modulating magnetic field 18 is selected to be of the order of magnitude of the characteristic field $B_c$ of the superparamagnetic particles used. The curvature of the magnetization characteristic lines (equation 3) follows the basic Langevin function:

$$\frac{d^2 L(x)}{dx^2} = -2\coth(x) \cdot (1 - \coth(x)^2) - \frac{2}{x^3} \quad (7)$$

with its maximum at x=1.37. Especially advantageous, therefore, is an amplitude of the modality magnetic field 18 of $\mu_0 H_a = 1.37 B_c$.

The frequency of the modulating magnetic field 18 for modulating the magnetization characteristic 5 is advantageously selected to be comparatively low, for example between 50 Hz and 100 Hz, so that for the generation of such low frequencies, coils with a high turn count and correspondingly low current and voltage, can be used. The scanning magnetic field 15 is selected advantageously to have a higher frequency, for example between 10 kHz and 100 kHz. Especially with the use with induction coils the magnetic field sensor 20 a higher frequency of the second magnetic field has the advantage that the voltage 24 induced in the measurement coil 20 and which is proportional to the frequency, will be high. Any static or steady state environmental direct field is advantageously selected to be as small as possible.

Figure 4:
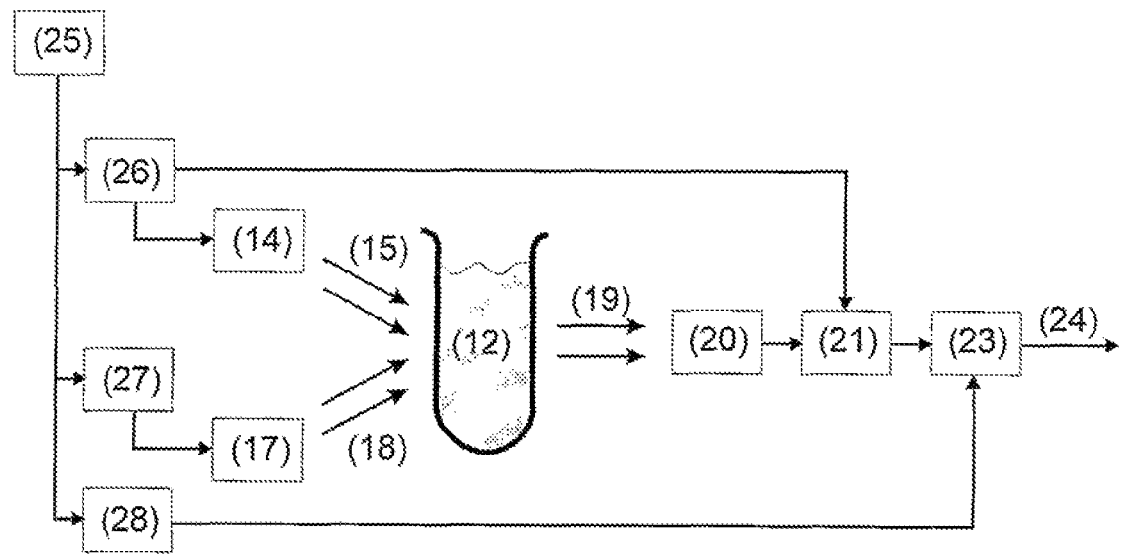

FIG. 4 sketches out an alternative device. A quartz oscillator 25 is used to generate a frequency which is divided by means of three frequency dividers 26, 27 and 28. The division ratio of the three dividers 26, 27 and 28 are so selected that they are respectively $$\frac{1}{l},$$
$$\frac{1}{m \cdot n}$$
$$\frac{1}{n}$$

with whole positive numbers l and n. The whole positive number m represents the multiple of the modulation frequency which is to be demodulated. Advantageously m will be even and in an especially advantageous case m will be selected to be equal to 2.

The field generators 17 and 14 produce modulation magnetic field 18 and the sensing magnetic field 15. The response magnetic field 19 is picked up by a differential, that is a gradiometric, induction coil serving as the magnetic field sensor. The coil is so constructed that it is composed of two identically fabricated but mutually oppositely wound, series-connected partial coils into only one of which the analyte in vessel 12 is immersed. In this manner it is possible advantageously to hold the parasitic effects of the direct induction of an electric voltage at the scanning frequency as low as possible so that the amplitude of the scanning magnetic field 15 can be selected to be very high without overdriving the preamplifier of the magnetic field sensor 20. In this manner an increase in the sensitivity of the apparatus can be achieved.

In addition the apparatus has a first phase sensitive detector 21 to which is applied the frequency of the scanning magnetic field 15 from the frequency divider 26 as a reference and which outputs the time course of the amplitude (see FIG. 2 elements 11 and 8) of the response magnetic field 19 at the frequency of the scanning magnetic field 15. These amplitudes 11 or 8 are searched by a second phase sensitive detector 23 for a frequency component which corresponds to the m-fold multiple of the frequency of the modulating magnetic field 18 for whole positive number m. The reference frequency in this case for the embodiment of FIG. 4 is supplied directly from a frequency divider 28 of the frequency of the oscillator 25 instead of from an oscillator as in the example of FIG. 3 where a frequency multiplier must be used. Advantageously, in this manner all three frequencies used are coupled in a fixed phase or phase correct manner so that any possible oscillator drift will not be significant for a measurement.

After the two phase sensitive detectors 21 and 23 the output voltage 24 is available as the measurement signal.

Figure 5:
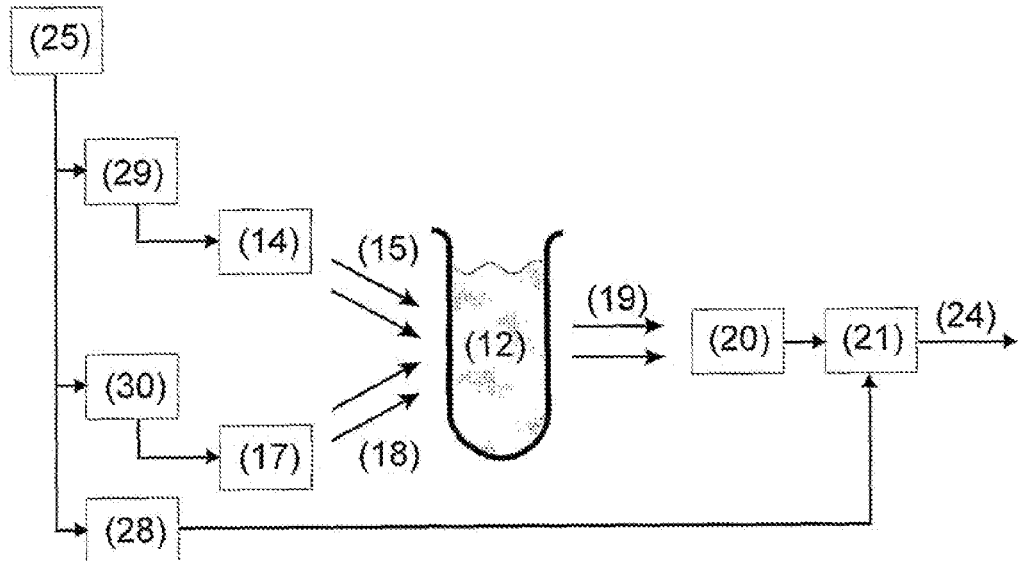

FIG. 5 sketches out a further device. A quartz oscillator is used as the frequency base which supplies three frequency dividers 29, 30 and 28. The divider ratios of the three dividers are so chosen that they are respectively $$\frac{1}{n+m}$$
$$\frac{1}{n(n+m)}$$
$$\frac{1}{n}$$

with whole positive numbers m and n. Here again m indicates the multiple of the modulation frequency. Advantageously m is even and in an especially advantageous manner is selected to be m=2. The device of FIG. 5 has only one phase sensitive detector 21 which is supplied with the frequency of the oscillator 25 divided by a factor n as the reference. This phase sensitive detector 21 outputs the time course of the same magnetic field component as in the two previously described embodiments of FIGS. 3 and 4.

Figure 6:
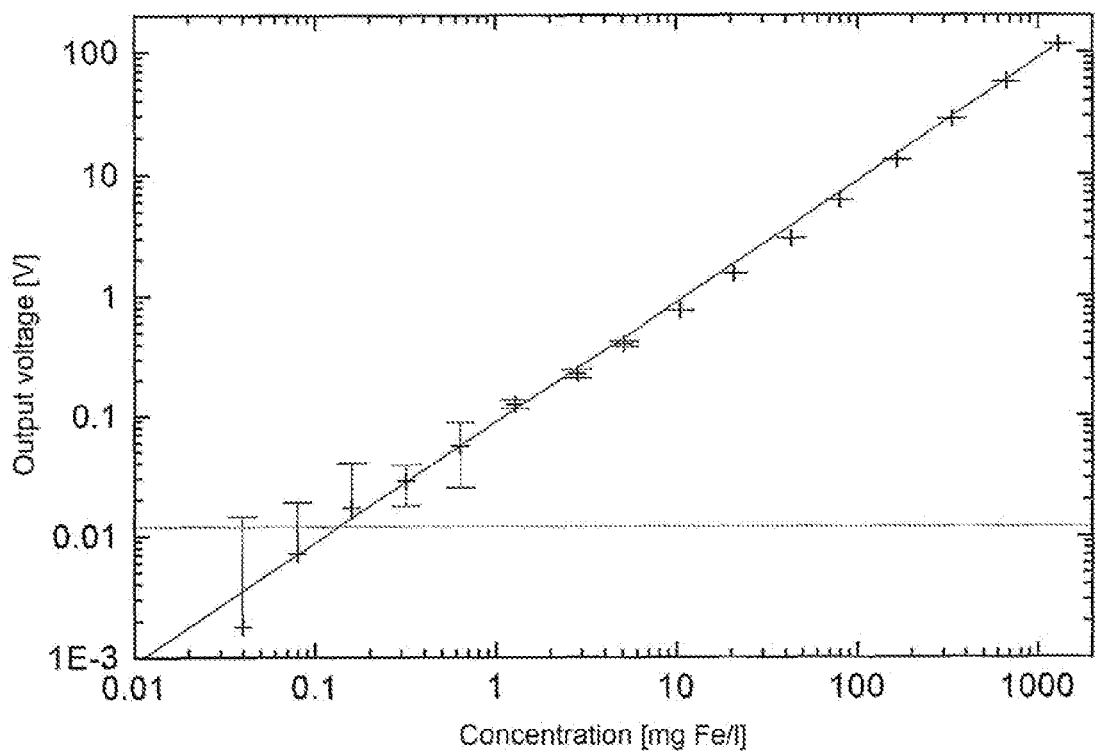
FIGS. 6, 7, and 8 are graphs illustrating the invention.

Experimentally, samples of different concentrations of magnetic particles were made and measured. For that purpose a solution of colloidal iron oxide particles in the nanometer size range was produced and serially diluted with isotonic table salt solution (NaCl). FIG. 6 shows the measured output voltage with standard deviation as a function of the iron concentration of the samples.

Figure 7:
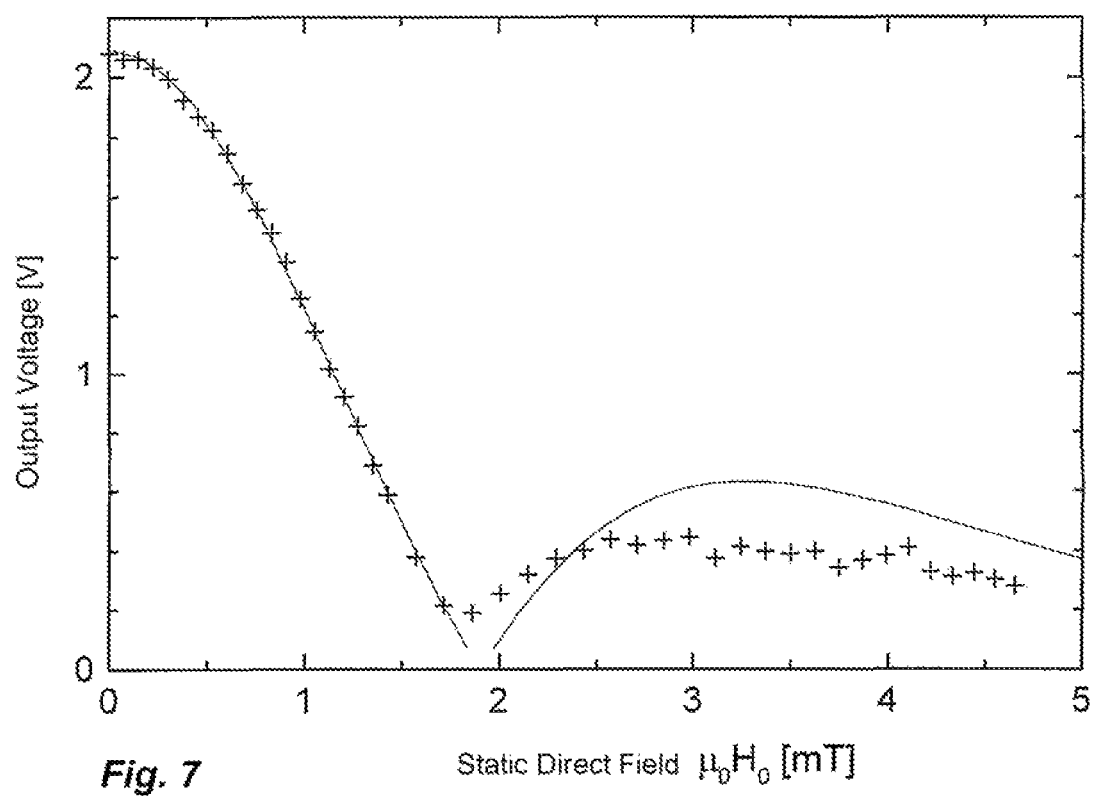

FIG. 7 shows how the measured signal of a sample of fixed concentration varies with a function of a static environmental direct field $H_o$. Maximum output voltage is obtained at a minimum direct field with a direct field amplitude of about 1.9 mT one observes a minimum of the output voltage. For higher direct fields the signal increases further. From the point of view of the mathematics, the signal follows the third derivative of the Langevin function $$\frac{d^3 L(x)}{dx^3} = -2(1 - \coth(x)^2)^2 + 4\coth(x)^2 \cdot (1 - \coth(x)^2) + \frac{6}{x^4} \quad (8)$$

In FIG. 7 this function is compared with the scaled amplitude and matched characteristic field value $B_c$=1.4 mT ($x=\mu_o H/B_c$). The agreement with measured values is found to be especially good for small static direct field $H_o$.

Figure 8:
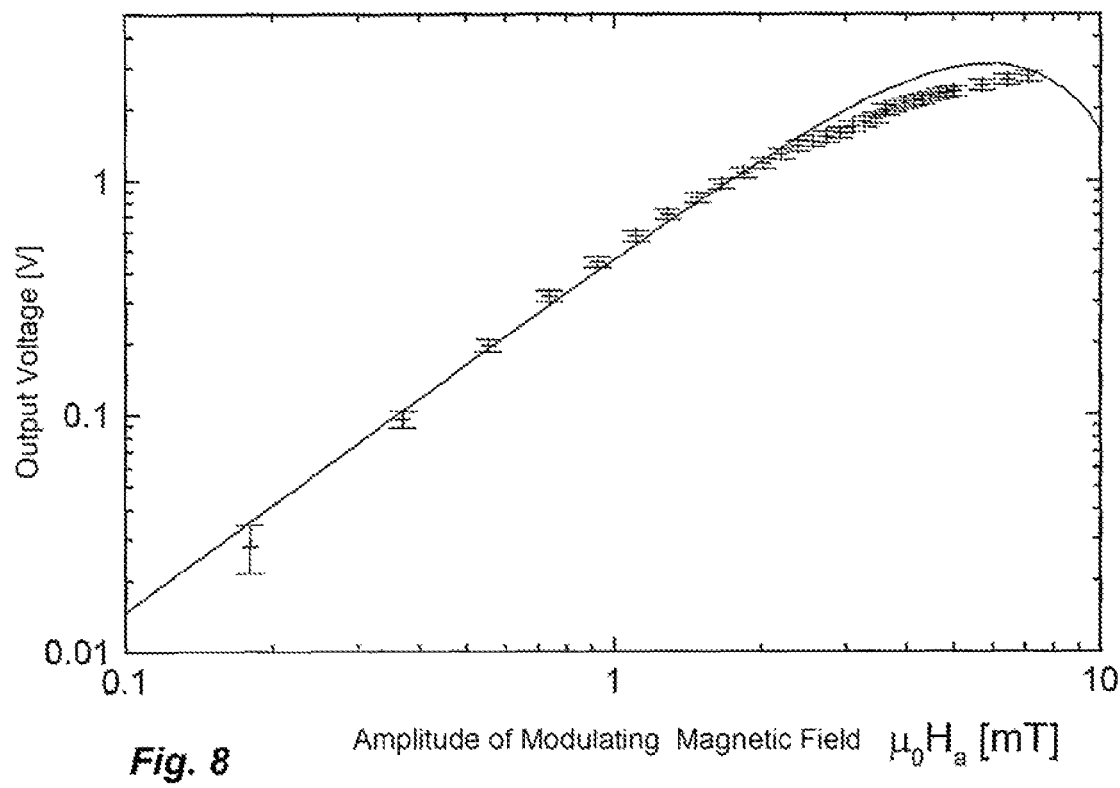

FIG. 8 shows the measured dependency of the output voltage of a sample of fixed concentration in dependence upon the amplitude of the modulating magnetic field. By integration over the amplitude dependent signal course, the signal was calculated and plotted in FIG. 8. The agreement with the measured value is especially good for low amplitudes.

The method/device can be used especially for the following purposes:

Detection of chemical substances, cells or viruses with respect to the quantitative determination of the molecular interaction, especially the Ligand-receptor interaction, the antigen-antibody interaction and interaction between oligonucleotides whereby superparamagnetic and/or ferromagnetic particles are coupled to the substances, cells or also viruses.

REFERENCE CHARACTER LIST 1, 4, 18 Modulating magnetic field
2 Magnetization characteristics, linear
3 Magnetic modulation induction for linear magnetization characteristics
5 Magnetization characteristics, nonlinear
6 Magnetic modulation induction for nonlinear magnetization characteristics
7 Additional scanning induction with linear magnetization characteristics
8 Amplitude of the magnetic induction at the frequency of the scanning magnetic field with linear magnetization characteristics
9, 10 Additional scanning induction with nonlinear magnetization characteristics for zero passages (9) and extremes (10).
11 Amplitude of the magnetic induction at the frequency of the scanning magnetic field with nonlinear magnetization characteristics
13, 16, 25 Oscillator
14, 17 Field generator
15 Scanning magnetic field
19 Response magnetic field
20 Magnetic field sensor
21, 23 Phase sensitive detectors
24 Output voltage
26, 27, 28, Frequency dividers
29, 30

The invention claimed is:

1. A device for the selective detection and/or quantification of super paramagnetic and/or ferromagnetic particles with analytes, the device comprising:
    a vessel for holding an analyte to be detected or to be quantified,
    at least one oscillator for producing an alternating modulating magnetic field of predetermined frequency and an alternating scanning magnetic field with a frequency different from that of the modulating magnetic field,
    at least one field generator connected to the oscillator for subjecting the analyte to the modulating magnetic field and to the scanning magnetic field at the same time,
    a magnetic field sensor for measuring a response magnetic field of the particles,
    a first phase-sensitive detector connected to the magnetic field sensor and responsive to the frequency of the amplitude of the response magnetic field at the frequency of the scanning magnetic field, and
    a second phase-sensitive detector connected to the first phase-sensitive detector.

2. The device according to claim 1 comprising at least one frequency divider for dividing the frequency of the oscillator.

3. The device according to claim 2 wherein the frequency divider divides the oscillator frequency in proportions of whole positive numbers.

4. The device according to claim 2, wherein the frequency dividers divide the oscillator frequency into the ratios $$\frac{1}{l},$$

$$\frac{1}{m \cdot n}, \text{ and}$$

$$\frac{1}{n},$$

where l, m, and n are positive whole numbers.

5. The device according to claim 4 wherein m is an even number.

6. The device according to claim 2 wherein the frequency dividers divide the oscillator frequency in the ratios of $$\frac{1}{(n+m)},$$

$$\frac{1}{n(n+m)}, \text{ and}$$

$$\frac{1}{n},$$

where m and n are positive whole numbers.

7. The device according to claim 2 with at least one frequency divider dividing the oscillator frequency into a reference frequency which is stored in at least one phase sensitive detector.

8. The device according to claim 7 in which a frequency from one frequency divider of the oscillator frequency is stored as a reference in the first phase-sensitive detector and a frequency from another frequency divider dividing the oscillator frequency is stored as a reference in the second phase-sensitive detector.

9. The device according to claim 2, wherein respective field generators are provided which are controlled by the frequencies of the frequency dividers.

10. The device according to claim 1 comprising at least one frequency multiplier.

11. The device according to claim 1, wherein the magnetic field sensor is configured as a differential field sensor.

12. The device according to claim 1, wherein the magnetic field sensor comprises two partial coils of the same construction type.

13. The device according to claim 12, wherein the partial coils of the magnetic field sensor are wound in opposite sensors.

14. The device according to claim 12 wherein the partial coils of the magnetic field sensor are connected in series.

15. The device according to claim 1, wherein the vessel with the analyte is in contact with only one of the two partial coils of the magnetic field sensor.

* * * * *